Figure 4:
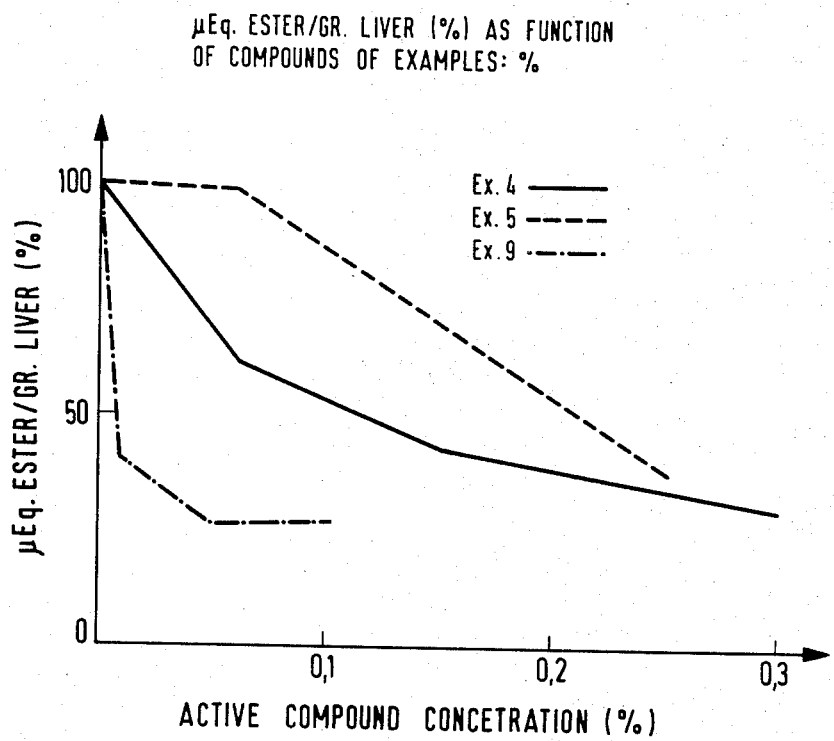

United States Patent [19]

Bar-Tana

[11] Patent Number: 4,634,795
[45] Date of Patent: Jan. 6, 1987

[54] LONG-CHAIN α,ω-DI-CARBOXYLIC ACIDS AND DERIVATIVES THEREOF AND PHARMACEUTICAL COMPOSITIONS CONTAINING THEM

[75] Inventor: Jacob Bar-Tana, Jerusalem, Israel

[73] Assignee: Epis S.A., Zug, Switzerland

[21] Appl. No.: 769,765

[22] Filed: Aug. 27, 1985

Related U.S. Application Data

[63] Continuation of Ser. No. 443,315, Nov. 22, 1982, abandoned.

[30] Foreign Application Priority Data

Dec. 15, 1981 [IL] Israel ........................................ 64542

[51] Int. Cl.$^4$ ...................... C07C 55/02; C07C 55/32; C07C 69/34; C07C 121/20
[52] U.S. Cl. .................................. 562/590; 558/442; 560/190; 560/192; 562/596; 564/198
[58] Field of Search ................ 560/190, 192; 562/590, 562/596; 260/465.4; 592/590, 596

[56] References Cited

U.S. PATENT DOCUMENTS

| | | | |
|---|---|---|---|
| 2,971,915 | 2/1961 | Borsoff et al. | 562/590 X |
| 3,678,102 | 7/1972 | Isard et al. | 560/190 X |
| 3,773,946 | 11/1973 | Creger | 424/318 |
| 3,776,951 | 12/1973 | Failey et al. | 562/590 |
| 3,930,024 | 12/1975 | Creger | 424/309 X |

OTHER PUBLICATIONS

Schisla et al.; J. Org. Chem., 35 (1970), pp. 3224–3230.
Beilstein; vol. 2; 2nd supp., (1942), p. 627, Springer-Verlog: Berlin.
Beilstein; vol. 2, 4th supp., (1976), pp. 2168, 2169, 2174, 2180, 2181, 2191 and 2192, Spinger-Verlog: Berlin.
Bouvier et al.; Bull. Soc. Chim. Fr. (1975), No. 9–10, pp. 2195–2201.

*Primary Examiner*—Joseph Paul Brust
*Attorney, Agent, or Firm*—Browdy and Neimark

[57] ABSTRACT

A novel class of compounds has been found to be effective in blocking cholesterol and neutral lipid synthesis in-vivo without adversely affecting energy metabolism. The active compounds have the general formula

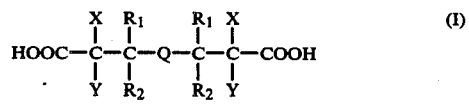

or in-vivo hydrolysable functional derivatives of the carboxylic groups thereof, wherein $R_1$ and $R_2$ each independently represents an unsubstituted or substituted hydrocarbyl or heterocyclyl radical;

X and Y each independently represent hydrogen, optionally substituted lower alkyl, halogen, cyano, carboxy, lower alkoxycarbonyl or carbamoyl; and Q represents a diradical consisting of a linear chain of 8 to 14 carbon atoms, one or more of which may be replaced by heteroatoms, said chain being optionally substituted by inert substituents and one or more of said carbon or heteroatom chain members optionally forming part of a ring structure.

The invention also provides pharmaceutical compositions comprising the aforementioned compounds of formula (I) for the treatment of obesity, hyperlipidemia and maturity-onset diabetes.

4 Claims, 8 Drawing Figures

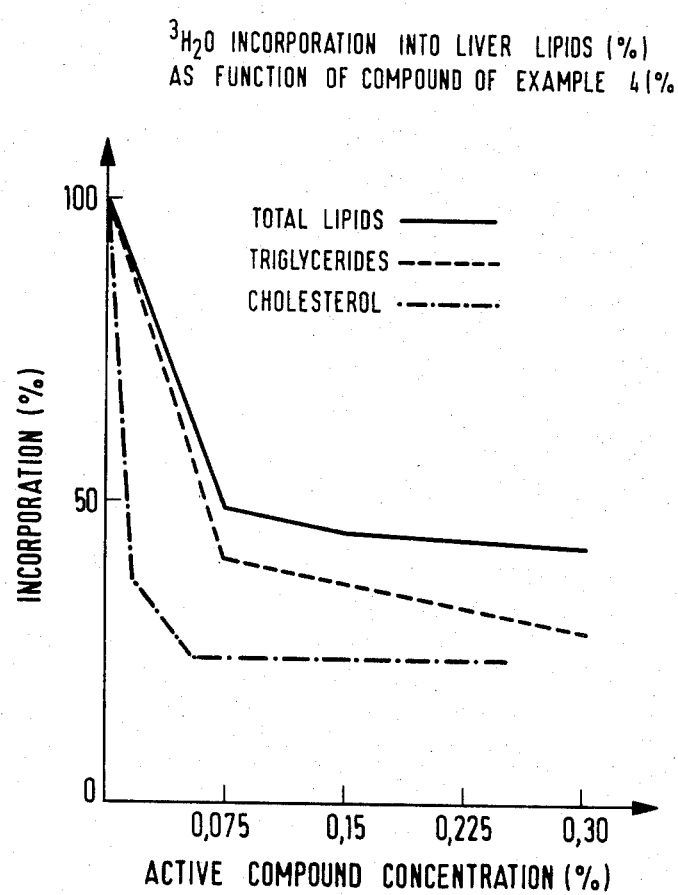

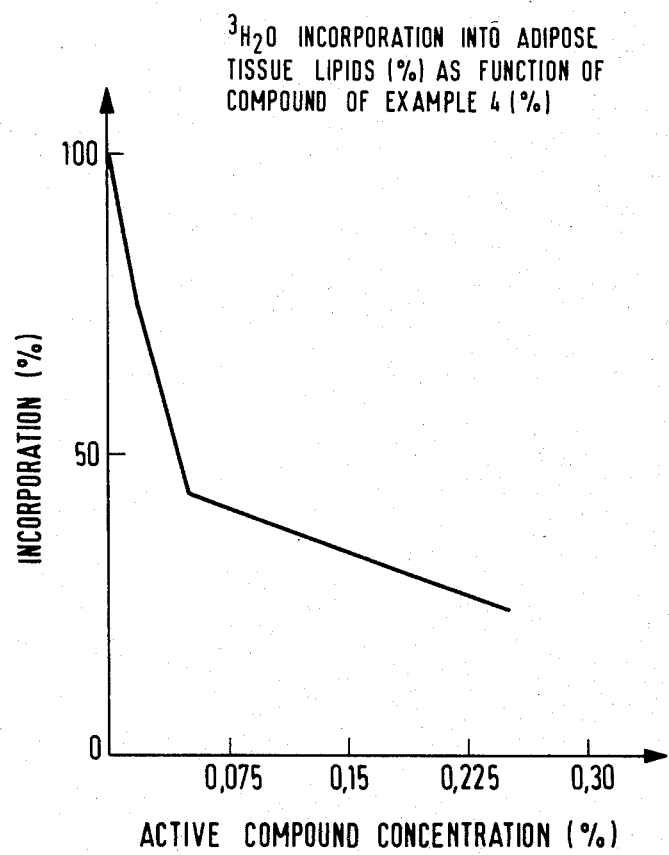

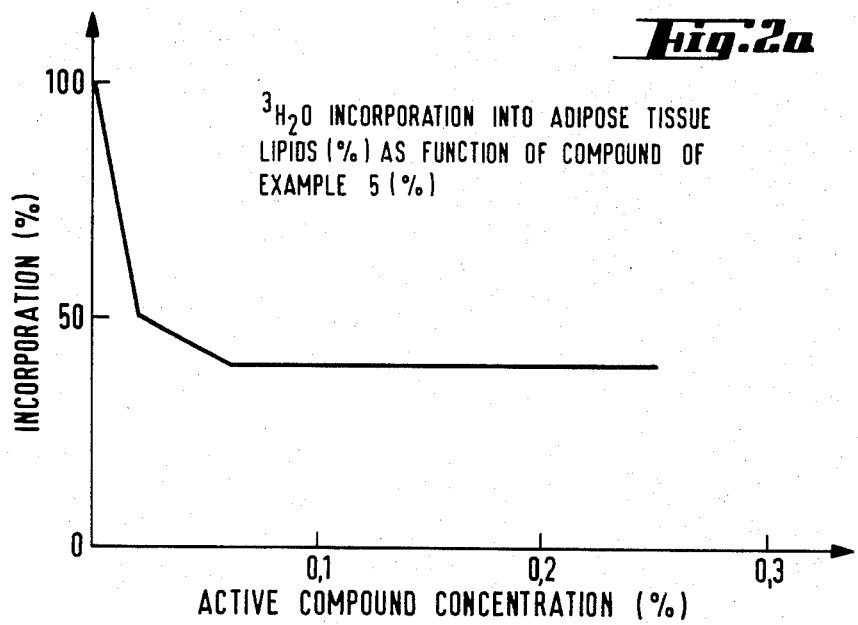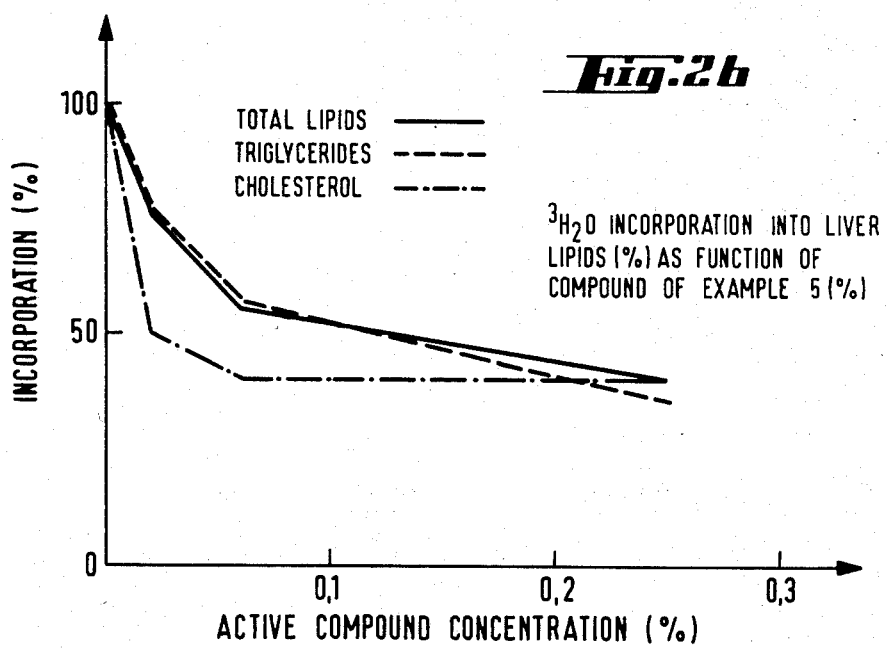

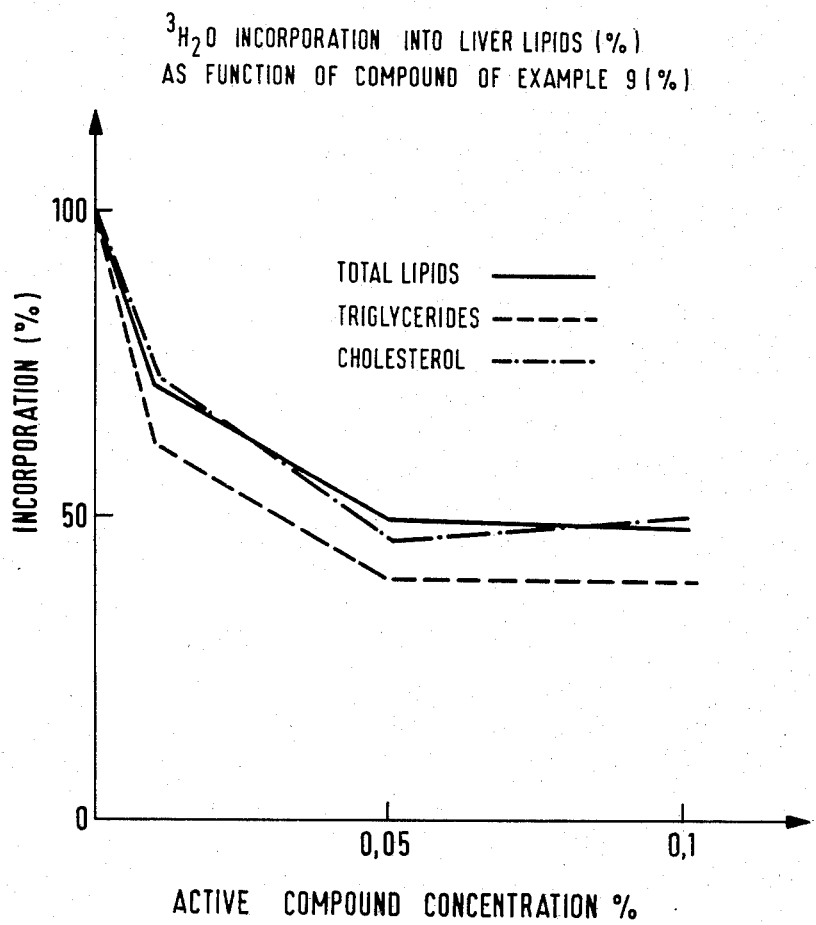

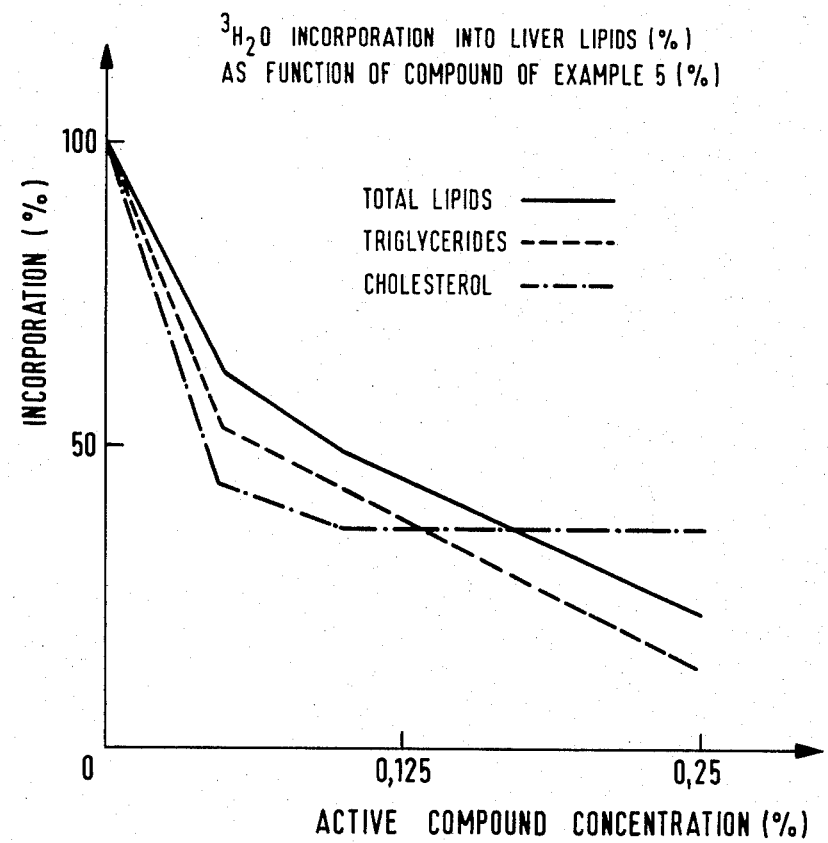

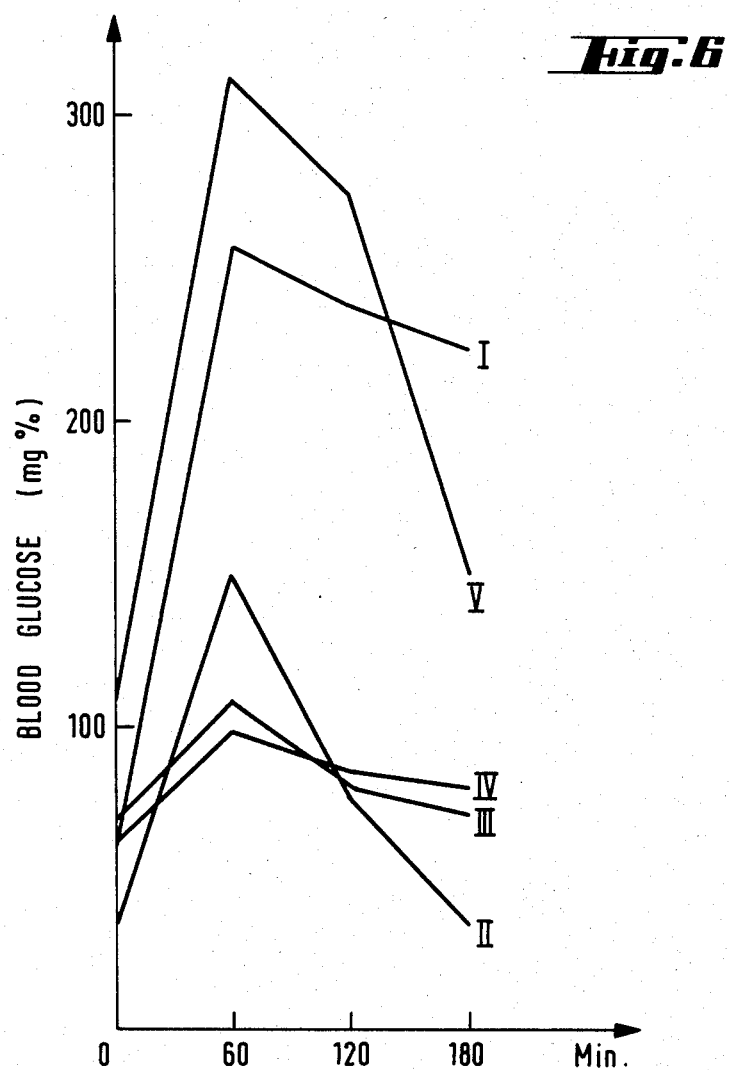

LONG-CHAIN α,ω-DI-CARBOXYLIC ACIDS AND DERIVATIVES THEREOF AND PHARMACEUTICAL COMPOSITIONS CONTAINING THEM

This application is a continuation of co-pending parent application Ser. No. 443,315, filed Nov. 22, 1982, now withdrawn in favor of the present application.

The present invention concerns novel derivatives of long-chain α,ω-dicarboxylic acids having valuable pharmacological activity in the treatment of obesity, hyperlipidemia and maturity-onset diabetes (insulin independent diabetes). The invention also provides pharmaceutical compositions comprising the aforementioned novel derivatives.

Obesity, hyperlipidemia and diabetes have been shown by epidemiological and other studies to play a causal role in atherosclerotic cardiovascular diseases which at present account for more than half of the total deaths in Western society. Thus, these pathological conditions may be regarded as leading factors affecting the mortality and morbidity of our society.

Obesity is still considered to be an "incurable disease", despite the recognized preventive value of weight reduction. Dietary measures were found in most studies to be ineffective for long term weight reduction and the effectiveness of behaviour modification in the treatment of obesity is still equivocal. A more drastic solution, a surgical ileojejunal shunt by-passing the small intestinal absorptive bed, is considered to be too risky a treatment for obesity. Nor did anorexic drugs prove to be a suitable solution to the problem, because these drugs are known to affect the central nervous system in a non-specific manner and their use has been drastically curbed by the Federal Drug Association.

The treatment of hypercholesterolemic-hypertriglyceridemic conditions is at present mainly based on low cholesterol dietary intake combined with drug treatment (mostly Clofibrate and its derivatives). However, recent indications of serious and sometimes lethal side effects of Clofibrate have resulted in disapproval of this drug in certain countries, leaving less efficient drugs as therapeutic alternatives.

Insulin-independent diabetes is well correlated with obesity, and overweight is considered to play a critical role in the polygenic etiology of peripheral insulin resistance. The classical pharmacological treatment of this diabetic state consists of increasing the serum insulin content either by insulin delivery or by stimulating insulin secretion. The ensuing hyperinsulinemia results in down-regulation of the insulin-resistant state. Hence, the treatment of insulin-independent diabetes should aim at alleviating insulin resistance with a concomitant normoinsulinemia and up-regulation of peripheral insulin receptors.

α,ω-dialkanoic acids of chain length of 10 to 14 carbon atoms which are tetra-methyl substituted on the α,α'-carbon atoms, as well as their salts and ester derivatives were disclosed in French Patent Publication No. 2,068,535 as possessing serum triglyceride-lowering activity and serum cholesterol-lowering activity. These known compounds, however, have not proved to be of value in medicine for the treatment of obesity and hypercholesterolemia. The corresponding β,β,β',β'-tetramethylalkanediols, derived from the former diacids by reduction, and their esters were disclosed in U.S. Pat. No. 3,930,024 and French Pat. No. 2,068,534 and alleged to have the same activities.

A novel class of compounds has now been found, in accordance with the present invention, to be surprisingly effective in blocking cholesterol and neutral lipid synthesis in-vivo without adversely affecting energy metabolism. The overall effect of these compounds in-vivo results in significant decrease in blood serum cholesterol and triglyceride levels and significant weight reduction due mainly to reduction of neutral lipid synthesis. The new compounds of the invention were also found to be beneficial for the alleviation of the diabetic trait in insulin-independent diabetes.

The novel compounds provided by the present invention have the general formula

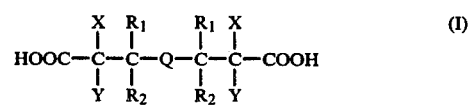

and in-vivo hydrolysable functional derivatives of the carboxylic groups thereof, wherein $R_1$ and $R_2$ each independently represents an unsubstituted or substituted hydrocarbyl or heterocyclyl radical; X and Y each independently represents hydrogen, optionally substituted lower alkyl, halogen, cyano, carboxy, lower alkoxycarbonyl or carbamoyl; and Q represents a diradical consisting of a linear chain of 8 to 14 carbon atoms, one or more of which may be replaced by heteroatoms, said chain being optionally substituted by inert substituents and one or more of said carbon or heteroatom chain members optionally forming part of a ring structure.

Included within the scope of the invention are those derivatives of the α and/or ω carboxy groups of the compounds of formula I above, which are capable of being hydrolised in-vivo to yield the free diacids of formula I. Among such suitable derivatives there should be mentioned, in the first place, salts with pharmaceutically acceptable inorganic or organic cations, in particular alkali metal salts, alkaline earth metal salts, ammonium salts and substituted ammonium salts; esters, particularly lower alkyl esters; amides, mono- and di-substituted amides; and anhydrides, e.g. with lower alkanoic acids; and lactones formed by ring closure of either or both carboxylic groups with a free hydroxy substituent (or substituents) in the molecule of formula (I).

The term "hydrocarbyl" in the definition of $R_1$ and $R_2$ includes, e.g., optionally substituted alkyl, alkenyl, alkynyl, cycloalkyl, optionally substituted aryl, optionally substituted aralkyl and the like.

A preferred group of compounds in accordance with the invention are those of formula (I) above in which $R_1$ and $R_2$ are each lower alkyl, Y is hydrogen and Q is a straight polymethylene chain of 8 to 14 carbon atoms; and in-vivo hydrolysable functional derivatives thereof.

Especially preferred compounds of the present invention are those of the general formula

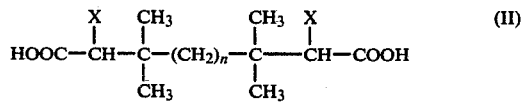

wherein X is hydrogen, lower alkyl, fluoro, chloro, bromo or cyano and n is an integer from 8 to 14; and their in-vivo hydrolysable functional derivatives.

The novel compounds of formula (I) according to the invention, can be prepared by methods known per se, some of which are illustrated in the examples herein.

In another aspect, the present invention provides pharmaceutical compositions for the treatment of obesity, hyperlipidemia and diabetes, comprising as active ingredients the novel compounds of formula (I) above together with pharmaceutical carriers or diluents. The pharmaceutical compositions are primarily for oral administration, but may also be for parenteral administration. These pharmaceutical compositions, which are preferably in dosage unit form, may be in the form of, e.g., tablets, capsules, lozenges, pills, powders and aqueous and non-aqueous solutions or suspensions. The pharmaceutical compositions of this invention preferably comprise also conventional pharmaceutical solid or liquid carriers or diluents, e.g., gelatin, sugars, starches, cellulose derivatives, fatty acids and their salts, vegetable oils, glycerine, glycols, water, aqueous saline or phosphate buffer solutions and the like. The compositions may also comprise other compatible substances normally used in pharmaceutical formulations and also other additives, such as colouring agents, flavouring agents and preservatives.

The pharmaceutical compositions according to the invention are preferably in dosage unit form, each unit containing from 50 to 500 mg of the active ingredient of the formula (I) above. The daily dosage of the compounds of formula (I) above according to the invention will depend on the age, needs and tolerance of the individual patient, but will usually range from 50 mg to from 5000 mg per day. The pharmacological activities of the compounds of formula (I) according to the invention could be demonstrated by means of in-vivo experiments in rats and *Psamomys Obesus* in accordance with standard methods. Some of these experiments are described hereinafter in detail and illustrated by the diagrams in the attached drawings.

I. EXPERIMENTS IN RATS IN VIVO

Rats that have previously been starved for 48 hours, were meal-fed or fed ad libitum a high carbohydrate, fat-free diet for 3–5 days, the diet being supplemented with the active compounds of formula (I) at dosages of 25–250 mg per Kg body weight per day. The biological effects in-vivo were evaluated by following the rate of incorporation of injected radioactive precursors (mainly $^3H_2O$) into liver and adipose tissue lipids and comparing the results observed with those obtained from groups of non-treated rats ("control groups"). Dose-response curves were plotted.

The hypolipidemic effect was followed by measuring the triglycerides and cholesterol content in serum of treated rats as compared to non-treated rats.

Experiment I(a)

Incorporation of $^3H_2O$ into neutral fat in liver and adipose tissue and into liver cholesterol in vivo $^3H_2O$ incorporation into liver and adipose tissue lipids in vivo was tested in rats fed a high carbohydrate diet ad libitum for three days, supplemented with varying proportions (in percent of the diet) of the active compounds of Examples 4, 5 and 9. $^3H_2O$ was then administered to the animals and the rates of incorporation of tritium (in $\mu$mole/gr/60 min) into various lipid fractions in liver and adipose tissue were determined and compared to the tritium incorporation under identical conditions in the control groups of rats.

The results are represented in FIGS. 1, 2 and 3 of the attached drawings showing the average tritium incorporation in the test animals as a percentage of the incorporation in the control group (taken as 100%).

The reduction in liver triglyceride content of rats fed with carbohydrate-rich diet supplemented with compounds of Examples 4, 5 and 9 (as compared to the control group=100%) is shown in FIG. 4 of the attached drawings.

Experiment I(b)

$^3H_2O$ incorporation into liver lipids in vivo (in $\mu$mole/gr liver) was tested in rats fed for 3 days a single daily meal of a high carbohydrate diet containing 0.25% of the active compound of Example 4. The results are shown in the following Table I.

TABLE I

| | $^3H_2O$ incorporation into liver total lipid, triglyceride and cholesterol ($\mu$mole/gr liver) | | |
|---|---|---|---|
| | Total Lipid | Triglyceride | Cholesterol |
| Non-treated (n = 5) | 157 ± 34 | 107 ± 21 | 2.7 ± 1.1 |
| Treated (n = 5) | 47 ± 5 | 19 ± 2 | 0.8 ± 0.2 |

Experiment I(c)

The procedure of Experiment I(b) was repeated for 5 days. The results are shown in the following Table II:

TABLE II

| | $^3H_2O$ incorporation into liver total lipid, triglyceride and cholesterol ($\mu$mole/gr liver) | | |
|---|---|---|---|
| | Total Lipid | Triglyceride | Cholesterol |
| Non-treated (n = 5) | 107 ± 18 | 71 ± 12 | 2.8 ± 0.8 |
| Treated (n = 5) | 53 ± 13 | 20 ± 7 | 1.4 ± 0.4 |

Experiment I(d)

A group of rats were meal-fed once daily for 3 days with a high carbohydrate, fat-free diet containing various percentages of the active compound of Example 5. $^3H_2O$ incorporation into liver lipids (total), triglycerides and cholesterol (as compared to the control group=100%) are shown in FIG. 5 of the attached drawings.

Experiment I(e)

Rats starved for 48 hours were fed a high carbohydrate, fat-free diet ad libitum for 3 or 5 days, supplemented with the active compound of Example 4 at the proportions shown in the following Table III. The serum lipids were determined in the treated rats and compared to a non-treated control group.

TABLE III

| | | Serum Lipids (mg %) | |
|---|---|---|---|
| | | Triglycerides | Cholesterol |
| | Non-treated (n = 8) | 41 ± 6 | 64 ± 10 |
| Active Compound | 0.06% (n = 5) | 15 ± 4 | 38 ± 5 |
| | 0.15% (n = 5) | 21 ± 4 | 32 ± 5 |
| | 0.25% (n = 5) | 15 ± 4 | 31 ± 3 |

Experiment I(f)

Rats starved for 48 hours were fed a high carbohydrate, fat-free diet supplemented with 0.25% of the active compound of Example 5 for 3 days ad libitum. The observed serum lipids are shown in the following Table IV.

TABLE IV

| | Serum Lipids (mg %) | |
|---|---|---|
| | Triglycerides | Cholesterol |
| Non-treated | 48 ± 6 (n = 9) | 80 ± 12 (n = 12) |
| Treated | 33 ± 3 (n = 9) | 40 ± 11 (n = 12) |

The observed serum lipoprotein profile as determined in this experiment is shown in the following Table V.

TABLE V

| | Non-treated | Treated |
|---|---|---|
| VLDL cholesterol (mg %) | 23.00 | 10.00 |
| LDL cholesterol (mg %) | 19.00 | 6.00 |
| HDL cholesterol (mg %) | 43.00 | 24.00 |
| HDL (VLDL + LDL) | 1.05 | 1.50 |

Experiment I(g)

The $LD_{50}$ of the active compound of Example 4 in rats was found to be >7 gr/Kg body weight (p.o.).

SUMMARY

The following conclusions were reached with regard to the biological effects of the active compound of Example 4, chosen as a representative active compound:

(a) The active compound was found to block the in vivo incorporation of $^3H_2O$ into neutral fat (diglycerides, triglycerides) in liver (80% inhibition at 250 mg/Kg body wt/day; 50% inhibition at 100 mg/Kg body wt/day), as well as in adipose tissue.

(b) The active compound was found to block the in vivo incorporation of $^3H_2O$ into cholesterol in liver (80% inhibition at 250 mg/Kg body wt/day; 50% inhibition at 100 mg/Kg body wt/day).

(c) Inhibition of neutral fat and cholesterol synthesis in liver exerted by the active compound resulted in an up to 60% decrease in serum glycerides and a 50% decrease in serum cholesterol, as well as a significant change in the serum lipoprotein profile.

(d) Inhibition of neutral fat synthesis in liver exerted by the active compound resulted in 30–50% decrease in the triglyceride content of the liver.

(e) It has been shown by a series of additional experiments on rats that the active compound does not affect the oxidation of glucose, palmitate or acetate to $CO_2$ in vivo.

II. Experiments with *Psamomys obesus*

*Psamomys obesus* were fed "Amrod 935" Purina Chow diet supplemented with 0.1% of the active compound of Example 4, ad libitum, for periods of 80 or 140 days. The biological effects of the active compound in vivo were evaluated as reported in the following experiments.

Experiment II(a)

Groups of young and old Psamomys were fed the above described diet for 140 and 80 days, respectively, whereafter the serum triglyceride and cholesterol levels were determined. The results are shown in the following Table VI.

TABLE VI

| | Serum Lipids (mg %) | |
|---|---|---|
| | Triglycerides | Cholesterol |
| Young animals: | | |
| Non-treated (n = 5) | 205 ± 29 | 65 ± 7 |
| Treated (n = 7) for 140 days | 62 ± 15 | 46 ± 7 |
| Old animals: | | |
| Non-treated (n = 5) | 220 ± 48 | 146 ± 6 |
| Treated (n = 5) for 80 days | 77 ± 35 | 92 ± 6 |

Experiment II(b)

The above experiment was repeated with groups of young and old Psamomys and the body weight determined. The results are shown in the following Table VII.

TABLE VII

| Young animals | Non-treated (n = 5) | Treated (n = 7) |
|---|---|---|
| Initial weight (gr) average | 100 ± 11 | 92 ± 19 |
| Weight gain (gr) average | 57 ± 33 | 36 ± 12 |
| Weight gain (gr) | 38, 38, 40, 55, 116 | 25, 29, 31, 32, 33, 38, 62 |
| Siblings' weight grain (gr) | a. 55 | 25, 33 |
| | b. 116 | 31, 38 |
| Old animals | Non-treated (n = 6) | Treated (n = 6) |
| Initial weight (gr) average | 246 ± 26 | 254 ± 52 |
| Weight gain (gr) average | 11 ± 13 | −26 ± 8 |

Experiment II(c)

Six *Psamomys obesus* fed Purina Chow diet ad libitum were selected for their diabetic trait by following their glucose tolerance test (GTT). The selected animals were then treated by feeding the same Purina diet supplemented with 0.1% of the active compound of Example 4 for periods varying between 30–70 days. The GTT was followed periodically throughout this period, as well as for 50 more days after the drug-supplemented diet had been replaced with the normal diet. A diagram of the GTT curves obtained with one representative animal is shown in FIG. 6 of the attached drawings. The GTT values for all six animals are shown in the following Table VIII as the sum of the glucose values observed at $0^h$, $1^h$, $2^h$, $3^h$.

TABLE VIII
GLUCOSE TOLERANCE TEST
SUM OF GLUCOSE VALUES AT 0, 1, 2, $3^h$.

| Psamomys | Pretreatment | Treatment | Elimination of Treatment |
|---|---|---|---|
| I | 779, 1082 | 364 | |
| II | 947, 980, 958 | 442 | |
| III | 790 | 296, 329, 326 | 849 |
| IV | 992 | 358, 336, 465 | 1049 |
| V | 867 | 434, 257, 388 | 470 |
| VI | 717 | 555, 555 | |

These results show that administration of the active compound of Example 4 resulted in correction of the GTT curve in 5 out 6 test animals, and that after termination of the treatment, the animals were found to revert to their original diabetic trait. Moreover, the serum insulin levels during the treatment period were found to be lower than 40 μm/ml, as compared to 40–200 μu/ml in the non-treated diabetic animals.

It is of interest to note that the active compound of Example 4 affects neither diabetes induced by steptozocin in rats, nor the GTT of nondiabetic Psamomys.

The preparation of some of the novel compounds of formula (I) according to the invention is illustrated in the following non-limiting Examples.

EXAMPLE 1

1,1,14,14-Tetra(ethoxycarbonyl)-2,2,13,13-tetramethyl-tetradecane

The bis-Grignard reagent prepared from 3.5 g of Mg turnings and 21.0 g of 1,10-dibromodecane in 90 ml of tetrahydrofuran (THF), was added dropwise by means of a syringe to a stirred suspension of 0.25 g of $Cu_2Cl_2$ and 25.0 g of diethyl isopropylidenemalonate in 50 ml of dry THF cooled to $-70°$ C. The reaction mixture was allowed to gradually reach room temperature under stirring and the stirring was continued at that temperature for 16 hours. The reaction mixture was then poured into a mixture of 100 ml of concentrated hydrochloric acid and 150 g of ice, under vigorous stirring, then diluted with water and extracted thrice with diethyl ether. The ether extracts were combined, washed with water and with a 10% solution of sodium carbonate and dried over anhydrous magnesium sulfate. The ether solution was filtered and evaporated to dryness. 34.0 g of the title compound were obtained and proved to be pure on thin layer chromatography.

NMR ($CDCl_3$): 4.17 (q, J=7 $H_z$, 8H); 3.30 (s, 2H); 1.27 (br.s, 32H); 1.10 (br.s, 12H).

EXAMPLE 2

1,1,16,16-Tetra(ethoxycarbonyl)-2,2,15,15-tetramethyl-hexadecane

The procedure of Example 1 was followed except that for the preparation of the bis-Grignard reagent 23.0 g of 1,12-dibromododecane were used instead of the dibromodecane.

The title compound was obtained in a yield of 25.0 g and gave a single spot on thin layer chromatography.

NMR ($CDCl_3$): 4.12 (q, J=8 $H_z$, 8H); 3.30 (s. 2H); 1.23 (br.s, 36H); 1.06 (br.s, 12H).

EXAMPLE 3

1,1,12,12-Tetra(ethoxycarbonyl)-2,2,11,11-tetramethyl-dodecane

The procedure of Example 1 was followed except that the bis-Grignard reagent was prepared from 17.0 g of 1,8-dibromooctane instead of the dibromodecane used in Example 1. 30.2 g of the title compound were obtained. On thin layer chromatography the product gave a single spot.

NMR ($CDCl_3$): 4.20 (q, J=8 $H_z$, 8H); 3.30 (s, 2H). 1.20 (br.s, 28H); 1.10 (br.s, 12H).

EXAMPLE 4

3,3,14,14-Tetramethyl-hexadecane-1,16-dioic acid

A mixture of 17.0 g of the tetra-ester of Example 1 and 300 ml of a 25% aqueous KOH solution was heated in an oil bath to reflux temperature and the mixture was refluxed until the organic phase has completely disappeared (about 48 hours). The aqueous solution was then cooled to room temperature, extracted with ether, further cooled by the addition of ice and acidified with concentrated aqueous hydrochloric acid, whereupon a solid precipitate was formed consisting of the corresponding tetracarboxylic acid. This solid precipitate was dissolved in diethyl ether and the solution dried over anhydrous magnesium sulfate, filtered and evaporated to dryness. The tetracarboxylic acid residue was decarboxylated by heating to 150°–160° C. on an oil bath until evolution of carbon dioxide was no longer observed. The crude product was cooled and recrystallized from a mixture of chloroform and petroleum ether (40°–60° C.). The pure product was obtained at a yield of 5.5 g.

NMR ($CDCl_3$): 11.06 (br.s, 2H); 2.23 (s, 4H); 1.28 (s, 20H); 1.03 (s, 12H).

EXAMPLE 5

3,3,16,16-Tetramethyl-octadecane-1,18-dioic acid

When the tetra-ester product of Example 2 is submitted to hydrolysis and decarboxylation by the procedure of Example 4, the title compound is obtained.

NMR ($CDCl_3$): 2.28 (s, 4H); 1.33 (s, 24H); 1.03 (s, 12H).

EXAMPLE 6

3,3,12,12-Tetramethyl-tetradeca-1,14-dioic acid

By the procedure of Example 4, the title compound is obtained from the tetra-ester prepared in accordance with Example 3.

NMR ($CDCl_3$): 2.28 (s, 4H); 1.33 (s, 16H); 1.07 (s, 12H).

EXAMPLE 7

1,14-Di-(ethoxycarbonyl)-,14-dicyano-2,2,13,13-tetramethyl-tetradecane

The procedure of Example 1 was followed except that instead of diethyl isopropylidenemalonate, there were used 19.1 g of ethyl isopropylidenecyanoacetate. The crude product was applied to the top of a dry column containing 1 kg of silica and eluted with 10% diethyl ether in petroleum ether (60°–80° C.). 30.1 g of the title compound were obtained.

NMR ($CDCl_3$): 4.252 (q, J=8 $H_z$, 4H); 3.370 (s, 2H); 1.297 (t, J=8 $H_z$, 6H); 1.275 (br.s, 20H) 1.143 (s, 6H); 1.107 (s, 6H).

I.R.: 2250, 1750 $cm^{-1}$

EXAMPLE 8

2,15-Dicyano-3,3,14,14-tetramethyl-hexadecane-1,16-dioic acid

The bis-cyano ester prepared in accordance with Example 7 was gently refluxed in a 10% aqueous KOH solution until the oil layer disappeared. The title compound was obtained in TLC purity.

NMR ($CDCl_3$): 7.88 (br.s, 2H); 3.46 (s, 2H); 1.25 (s, 20H); 1.11 (br.s, 12H);

IR: 2260, 1730 $cm^{-1}$

EXAMPLE 9

2,15-Dibromo-3,3,14,14-tetramethyl-hexadecane-1,16-dioic acid 3,3,14,14-Tetramethyl-hexadecane-1,16-dioic acid prepared as described in Example 4 was dissolved in 2 ml of dry CCl$_4$ and 5.8 ml of SOCl$_2$ were added. The mixture was heated to 65° C. for 30 minutes, cooled to room temperature and 10 ml of additional dry CCl$_4$ were added, followed by 2 drops of 48% hydrobromic acid and, slowly, 4.3 g of N-bromo-succinimide (NBS). The mixture was heated for 10 minutes at 70° C. and thereafter for one more hour at 85° C. The reaction mixture was cooled, filtered and evaporated to dryness. The crude bis-(alpha-bromoacid chloride) product was added dropwise to a 10% aqueous solution of KOH, the solution was stirred for 1 hour and then acidified and extracted thrice with diethyl ether. The ether extracts were combined, dried over anhydrous magnesium sulfate and filtered. Evaporation to dryness yielded the crude title compound which was purified on preparative thin layer chromatography plates (silica), developed with 3% methanol in methylene dichloride.

1.5 g of the pure title compound were obtained.

NMR (CDCl$_3$): 8.65 (br.s, 2H); 4.21 (s, 2H); 1.33 (br.s, 20H); 1.15 (s, 12H).

IR: 1750, 1140, 1010, 725, 660 cm$^{-1}$.

EXAMPLE 10

2,3,3,14,14,15-Hexamethyl-hexadecane-1,16-dioic acid 70 ml of a 15% solution of n-butyllithium in hexane was added dropwise by a syringe to a stirred mixture of 70 ml of THF and 14 ml of redistilled diisopropylamine, at −20° C. under a nitrogen atmosphere. After stirring for 30 minutes, 7.5 g of 3,3,14,14-tetramethylhexadecane-1,16-dioic acid (prepared in Example 4) in 10 ml of dry THF were added to the reaction mixture, the temperature being maintained below −10° C. The reaction mixture was allowed to warm slowly to 50° C. and maintained at that temperature for 2 hours, thereafter cooled to −20° C. and 5.4 g of methyl iodide were added at such a rate as to keep the temperature below 0° C. The reaction mixture was then heated to 40° C. for one hour and then poured into an ice cold 10% solution of hydrochloric acid. The mixture was extracted twice with methylene chloride, washed with 10% aqueous hydrochloric acid and with water and dried over anhydrous magnesium sulfate. The crude product was purified by chromatography on a silica column the eluent being a 3% solution of methanol in methylene chloride.

NMR (CDCl$_3$): 11.33 (br.s, 2H); 2.43 (q, J=8 H$_z$, 2H); 1.25 (br.s, 20H); 1.13 (d, J=8 H$_z$, 6H); 0.91 (s, 12H).

EXAMPLE 11

1,14-Diethoxycarbonyl-2,2,13,13-tetramethyl-tetradecane 3.42 g of 3,3,14,14-tetramethylhexadecane-1,16-dioic acid were converted to the corresponding diacid chloride by reaction with 5.8 ml of SOCl$_2$ and the crude diacid chloride was added under stirring to 30 ml of absolute ethanol. The solution was evaporated to dryness whereupon 3.4 g of the title compound were obtained.

NMr (CDCl$_3$): 4.13 (q, J=7 H$_z$, 4H); 2.23 (s, 4H); 1.30 (s, 26H); 1.00 (s, 12H).

IR: 1735, 760 cm$^{-1}$.

EXAMPLE 12

1,14-Di-(ethoxycarbonyl)-1,14-dibromo-2,2,13,13-tetramethyl-tetradecane

The title compound was prepared by the procedure of Example 11 from the bis-acid chloride of the α,α'-dibromoadiacid of Example 9.

NMR (CDCl$_3$): 4.20 (s, 2H); 3.73 (s, 6H); 1.27 (s, 20H); 1.07 (s, 12H).

EXAMPLE 13

1,14-Bis-carbamoyl-2,2,13,13-tetramethyl-tetradecane

The bis-acid chloride of 3,3,14,14-hexadecane-1,16-dioic acid, prepared as described in Example 11 was added under stirring to an ice-cold saturated solution of ammonia in dry methanol. 3.3 g of the bis-amide title compound were obtained.

NMR (CDCl$_3$): 5.43 (br.s, 4H); 2.10 (s, 4H); 1.30 (s, 20H); 1.00 (s, 12H).

IR: 3440, 3190, 1660, 1625 cm$^{-1}$.

I claim:

1. A compound of the formula

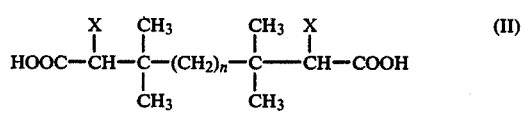

(II)

wherein X is hydrogen, lower alkyl, fluoro, chloro or bromo, and n is an integer from 8 to 14; or a lower alkyl ester, alkali metal salt, alkaline earth metal salt or a NH$_4$ salt thereof; with the proviso that when X is hydrogen, then n is other than 8.

2. A compound selected from:
3,3,14,14-tetramethyl-hexadecane-1,16-dioic acid;
3,3,16,16-tetramethyl-octadecane-1,18-dioic acid;
2,15-dibromo-3,3,14,14-tetramethyl-hexadecane-1,16-dioic acid;
2,3,3,14,14,15-hexamethyl-hexadecane-1,16-dioic acid;
1,14-diethoxycarbonyl-2,2,13,13-tetramethyl-tetradecane;
1,14-di(ethoxycarbonyl)-1,14-dibromo-2,2,13,13-tetramethyl-tetradecane.

3. A compound according to claim 1, wherein X is hydrogen or lower alkyl.

4. A compound according to claim 3, which is 3,3,14,14-tetramethyl-hexadecane-1,16-dioic acid.

* * * * *